Figure 1:
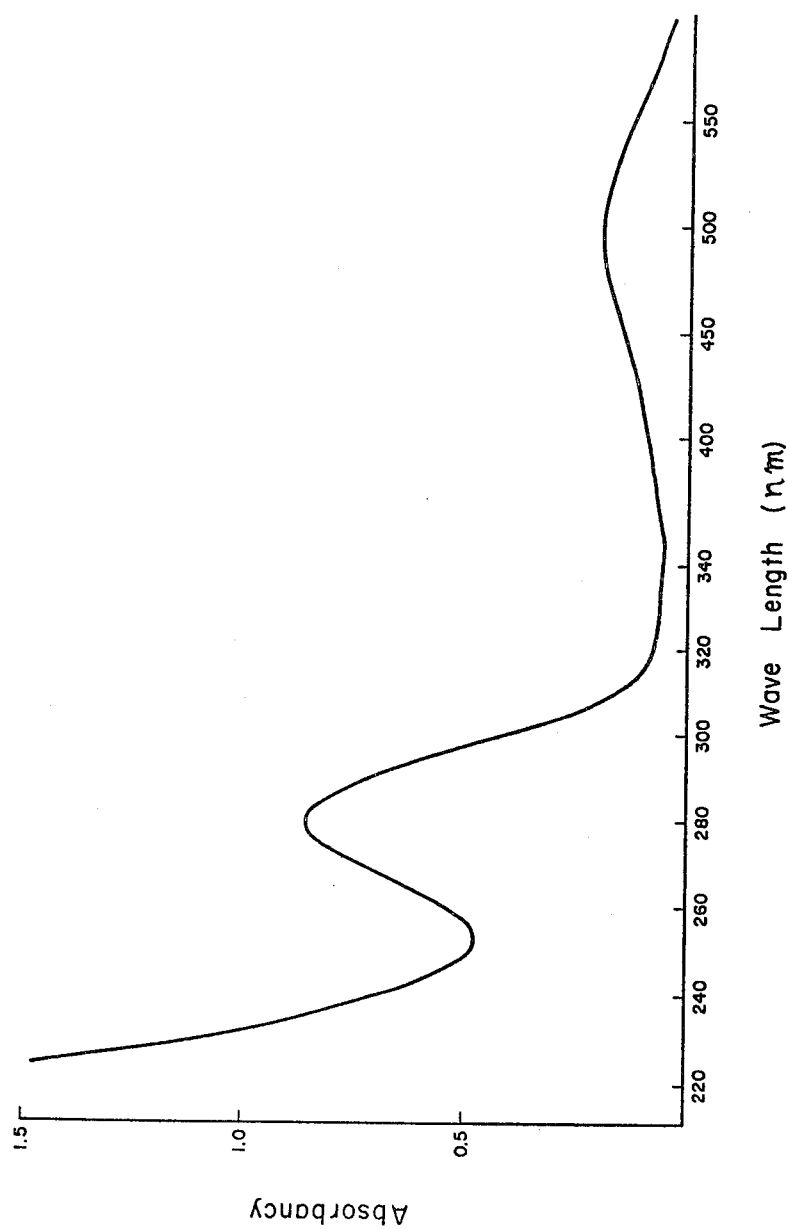

United States Patent [19]

Higashide et al.

[11] 4,298,600

[45] Nov. 3, 1981

[54] ANTIBIOTIC C-14482 $A_1$ AND METHOD FOR PRODUCING SAME

[75] Inventors: Eiji Higashide, Takarazuka; Seiichi Tanida, Kyoto; Masayuki Muroi, Naganohigashi; Mitsuko Asai, Takatsuki, all of Japan

[73] Assignee: Takeda Chemical Industries, Ltd., Japan

[21] Appl. No.: 930,317

[22] Filed: Aug. 2, 1978

[30] Foreign Application Priority Data

Aug. 4, 1977 [JP] Japan ............................. 52-93875

[51] Int. Cl.³ .............................................. C12P 1/04
[52] U.S. Cl. .................................. 424/120; 424/119; 435/170; 435/872
[58] Field of Search ................. 424/120, 119; 435/170

[56] References Cited

U.S. PATENT DOCUMENTS 3,923,977  12/1975  Aoki et al. ..................... 435/128

*Primary Examiner*—Alvin Tanenholtz
*Attorney, Agent, or Firm*—Wenderoth, Lind & Ponack

[57] ABSTRACT

A novel antibiotic C-14482 $A_1$ is produced by cultivating a microorganism belonging to the genus Nocardia and capable of producing Antibiotic C-14482 $A_1$ in a culture medium, whereby Antibiotic C-14482 $A_1$ is elaborated and accumulated in the culture medium, and recovering the same antibiotic.

Antibiotic C-14482 $A_1$ is useful as a germicide or disinfectant.

2 Claims, 2 Drawing Figures

4,298,600

ANTIBIOTIC C-14482 A₁ AND METHOD FOR PRODUCING SAME

This invention relates to Antibiotic C-14482 $A_1$ (- hereinafter sometimes referred to briefly as C-14482 $A_1$) which is a novel antibiotic and a method for producing said antibiotic. The present inventors collected samples from the natural kingdom including a large variety of soil samples and undertook screenings of the microorganisms isolated from such samples for the antibiotics which they might produce. This exploration and investigation resulted in the discoveries, that a certain microorganism is able to produce a novel antibiotic, that this microorganism belongs to the genus Nocardia and that cultivating said microorganism in a suitable nutrient medium under controlled fermentation conditions results in an accumulation of said antibiotic in the cultured broth. These findings were followed by further research, which has culminated in this invention.

This invention is, therefore, concerned with:

(1) Antibiotic C-14482 $A_1$ which has the following properties:

(I) Elementary analysis: (%): C, 58.02, 59.18; H, 5.84, 5.70; N, 16.32, 17.14.
(II) Melting point: Not less than 300° C.
(III) Specific rotation: $[\alpha]_D^{24.5} + 150° \pm 30°$ (c=0.05, ethanol)
(IV) Ultraviolet absorption spectrum:
  $\lambda_{max}^{MeOH}$ ($E_{1cm}^{1\%}$) 214 nm±2(503±50)
  $\lambda_{max}^{MeOH}$ ($E_{1\,cm}^{1\%}$) 281 nm±2(209±10)
  $\lambda_{max}^{MeOH}$ ($E_{1\,cm}^{1\%}$) 498 nm±2(46.0±5)
(V) Infrared absorption spectrum (KBr): Principal peaks (cm⁻¹): 3430, 3175, 2940, 2890, 2850, 1680, 1650, 1625, 1600, 1455, 1390, 1345, 1250, 1170, 1140, 1110, 1075, 1025, 995, 935, 910, 825
(VI) Solubility:
  Practically insoluble: Hexane, petroleum ether.
  Sparingly soluble: Ethanol, butanol, ethylacetate, water.
  Soluble: Methanol, chloroform.
(VII) Color reactions: Negative: Sakaguchi reaction, Barton reaction. Potassium permanganate decolorized.
(VIII) Acidity, neutrality or basicity: Weakly basic.
(IX) Color of crystals: Dark red to reddish brown.
(X) Molecular weight: $4.6 \times 10^2$ (measured by Vapor pressure osmometry in $CH_3COOC_2H_5$)

(2) a method for producing Antibiotic C-14482 $A_1$ characterized by cultivating a microorganism which belongs to the genus Nocardia and is capable of producing Antibiotic C-14482 $A_1$ in a culture medium to have Antibiotic C-14482 $A_1$ elaborated and accumulated in the cultured broth and recovering the same antibiotic. and (3) A substantially pure culture of the microorganism belonging to the genus Nocardia having the characteristics identifiable with those of ATCC-31309, said culture being capable of producing, in a culture medium containing assimilable carbon and digestible nitrogen sources, a recoverable amount of Antibiotic C-14482 $A_1$.

In the present method for the production of Antibiotic C-14482 $A_1$, any microorganisms which belong to the genus Nocardia and are capable of producing Antibiotic C-14482 $A_1$ can be employed. In the present specification these microorganisms are en bloc referred to briefly as C-14482 $A_1$-producing strain.

As the typical example of the microorganism employable in the present method for the production of Antibiotic C-14482 $A_1$, strain No. C-14482, which was isolated by the present inventors in the course of the search for antibiotic producers, is mentioned.

The present inventors investigated microbiological characteristics of strain No. C-14482 by procedures analogous to the method of Schirling and Gottlieb (International Journal of Systematic Bacteriology 16,313–340, 1966). The results obtained by cultures of the microorganism at 28° C. for 21 days are as follows.

(1) Morphological characteristics

The vegetative mycelium is colorless to pale yellow or orange yellow and develops well with branches both on agar and in liquid media.

The vegetative mycelium measures 0.5 to 1.2 μm in diameter for the most part and, in late phases of the cultivation, divides itself into fragments resembling rod bacteria or elongated rod bacteria or branched hyphae. This strain gives good growth on various taxonomic media and while the aerial mycelia well develop on the vegetative mycelium, the former appears in many cases as if it had grown on a large number of coremia-like bodies (50–180 μm×400–1500 μm). Many of aerial hyphae are flexuous or straight but some appear to be loosely spiral or branching on but rare occasions. Microscopic examination of aged cultures reveals that in few cases do the spores occur in chains, there being few of what are called conidia or spores. When examined under a microscope, cells taken from the surface of such a culture revealed the presence of many elongated ellipsoidal (0.5–1.2 μm×4.8–6.8 μm) and ellipsoidal (0.8–1.2 μm×1.5–4 μm) cells which looked like fragmented cells or arthrospores, the surfaces of which were smooth as examined by electron microscopy.

The aerial mycelium is generally sparse and although fair growth is noted on many media over 3 to 7 days of incubation, it sometimes disappears as cultivation is carried out for 7 to 10 days.

When cultivated in liquid media, the microorganism shows motility in a growing phase when the mycelia show polymorphism, i.e. the forms of rod, branched cells thereof or elongated rod, either as they are independent, in chains or branched. Electron microscopic examination shows a large number of elongated flagella around the cells.

(3) The constituents of cells

The strain was shake-cultured in modified ISP No. 1 medium at 28° C. for 66 to 90 hours and in the well-grown stationary phase, the cells were collected and rinsed. By the method of B. Becker et al. [Applied Microbiology 12, 421 (1964)] and the method of M. P. Lechevalier. [Journal of Laboratory and Clinical Medicine 71, 934 (1968)], the above cells were examined for diaminopimelic acid and sugar composition. The former was found to be the meso-form and, as to the latter, spots corresponding to galactose and arabinose, respectively, were observed. According to the method of B. Becker et al (Applied Microbiology 17, 236, 1965) cell walls were collected and analyzed for diaminopimelic acid, sugar and amino acids. Regarding diaminopimelic acid, its meso-form was detected. However, while a large amount of galactose was in evidence as the constituent sugar, there was no evidence of arabinose. As to amino acids, glutamic acid and alanine were clearly detected, although lysine and glycine could be found only in traces.

(3) Cultural Characteristics on Taxonomical Media

The strain gives comparatively good growth invariably on various media and the color of the vegetative mycelium is colorless to pale yellow in early phases of incubation but is pale yellowish brown to yellow brown hues in later stages. The organism does not produce soluble pigments in most taxonomical media but produces a faint brown pigment in a few media. The aerial mycelium is powdery, generally moderate and white to yellow or pale yellowish brown. The aerial mycelium disappears on many media on prolonged culture (approximately 2 weeks or longer), with the surface of vegetative mycelium beginning to become glossy. The cultural features of this particular strain are summarized in Table 1.

Table 1

Cultural characteristics of strain No. C-14482 on taxonomical media (A) Sucrose nitrate agar:
  Growth (G): Poor, thin, colorless
  Aerial mycelium (AM) Sparse, white
  Soluble pigment (SP): None
(B) Glucose nitrate agar
  G: Poor, thin, colorless
  AM: Very sparse, white
  SP: None
(C) Glycerol nitrate agar:
  G: Moderate, colorless to Lt Melon Yellow or Colonial Yellow Maize (3 ea or 2 ga)* or Brite Melon Yellow (3 ia)*, coremia-like bodies formed.
  AM: Very sparse, white to Lt Melon Yellow (3 ea)*
  SP: None
(D) Glucose asparagine agar
  G: Moderate, colorless to Melon Yellow (3 ga)*
  AM: Sparse, Lt Melon Yellow (3 ea)*
  SP: None
(E) Glycerol asparagine agar:
  G: Moderate, colorless to Melon Yellow (3 ga)*
  AM: Moderate, white to Lt Wheat (2 ea)*
  SP: None
(F) Nutrient agar:
  G: Moderate, colorless to Lt Ivory (2 ca)* or Melon Yellow (3 ga)*
  AM: None
  SP: None
(G) Calcium malate agar:
  G: Moderate, colorless to Melon Yellow (3 ga)* or Brite Marigold (3 pa)*; coremia-like bodies formed.
  AM: Sparse, white
  SP: None
(H) Yeast extract-malt extract agar:
  G: Luxuriant, colorless to Melon Yellow (3 ga)* or Brite Maize (3 la)*; coremia-like bodies formed.
  AM: Moderate, white to Pearl Pink (3 ca)* or Lt Melon Yellow (3 ea)*
  SP: Pale yellowish brown
(I) Oatmeal agar:
  G: Moderate, colorless to Melon Yellow (3 ga)* or Lt Ivory (2 ca)*
  AM: Moderate, white to Lt Melon Yellow (3 ea)* or Pearl Pink (3 ca)*
  SP: None or pale yellowish brown
(J) Starch agar:
  G: Moderate, colorless to Melon Yellow or Colonial Yellow Maize (3 ga or 2 ga)*
  AM: Sparse, white to Lt Melon Yellow (3 ea)*
  SP: None
(K) Peptone yeast extract iron agar:
  G: Moderate, colorless to Beige Brown (3 ig)* or Brite Maize (3 la)*
  AM: None or sparse, white
  SP: Pale yellowish brown
(L) Tyrosine agar:
  G: Moderate, colorless to Beige Brown (3 ig)* or Brite Maize (3 la)*; coremia-like bodies formed.
  AM: Sparse, Pearl Pink (3 ca)* or Brite Maize (3 la)*
  SP: Light yellowish brown (a tinge of purple)

* The color codes according to Color Harmony Manual, 4th ed. (Container Corporation of America, 1958)

(4) Physiological characteristics

The physiological characteristics of the strain are shown in Table 2. Temperature range for the growth: 12° C. to 38° C. The temperature range for which the aerial mycelia grow on agar (ISP No. 2) is 20° to 35° C.

Table 2: The physiological characteristics of strain No. C-14482

Temperature range for the growth: 12° to 38° C.
Temperature range for the growth of the aerial mycelia: 20° to 35° C.
Liquefaction of gelatin: Very weak
Hydrolysis of starch: Positive
Reduction of nitrates: Positive
Peptonization of milk: Positive
Coagulation of milk: Negative
Decomposition of casein: Positive
Production of melanoid pigments:
  (peptone yeast extract iron agar): Negative
  (tyrosine agar): Negative
Decomposition of tyrosine: Positive
Decomposition of xanthine: Negative
Decomposition of hypoxanthine: Negative
Tolerance to lysozyme: Positive
Tolerance to sodium chloride: 2%

(5) Utilization of various carbon sources

The utilization of various carbon sources was investigated using a medium described by Pridham and Gottlieb [Journal of Bacteriology 56, 107 (1948)] and a basal medium of the same composition plus 0.1% of yeast extract (Difco Co.). The results are shown in Table 3.

TABLE 3

| The utilization of carbon sources by strain No. C-14482 | | |
|---|---|---|
| Source of carbon | Growth | |
| D-Xylose | + | ++* |
| L-Arabinose | − | + |
| D-Glucose | ++ | ++ |
| D-Galactose | ++ | ++ |
| D-Fructose | +++ | +++ |
| L-Rhamnose | ++ | + |
| D-Mannose | ++ | +++ |
| Sucrose | ++ | ++ |
| Lactose | ± | − |
| Maltose | + | ++ |
| Trehalose | ++ | ++ |
| Raffinose | ± | − |
| Melibiose | ± | ± |
| i-Inositol | − | ± |
| D-Sorbitol | − | ± |
| D-Mannitol | ++ | ++ |
| Glycerol | ++ | +++ |
| Soluble starch | + | ++ |

TABLE 3-continued

| The utilization of carbon sources by strain No. C-14482 | |
| --- | --- |
| Source of carbon | Growth |
| Control | — — |

*Basal medium with 0.1% yeast extract
Note:
+ + +: Luxuriant growth
+ +: Good growth
+: Growth
±: Poor growth
−: No growth (6) Other characteristics The cells were harvested by the procedure previously described in "(2) The constituents of cells" and DNA was prepared by a procedure analogous to that of J. Murmar et al. [Journal of Molecular Biology, 3, 208, 1961]. The G-C (Guanine-Cytosine) content of the DNA was found to be about 71 mole %.

Gram-staining of the vegetative mycelium of this strain was positive.

The above characteristics of strain No. C-14482 were compared with the descriptions in S. A. Waksman's "The Actinomycetes Vol. 2" [The Williams and Wilkins Co., 1961]; R. E. Buchanan and N. E. Gibbons, "Bergey's Manual of Determinative Bacteriology, 8th ed., 1974"; and other literature references.

The above observations that (1) the strain in later phases of incubation is fragmented into the shapes of rod or elongated rods, or branched cells thereof, (2) it gives few well-defined conidia or spores, (3) the surfaces of its colonies on agar are leathery and, in many cases, are glistening like bacterial colony and (4) the G-C content of the mycelium is about 71 mole %, coupled with other characteristics, suggest that the strain might belong to Group III of the genus Nocardia. However, in view of our inability to find any known strain of microorganism which shared all of the above cultural characteristics, physiological characteristics, cell motility, cell wall composition, etc. with our present strain, we identified this strain as a novel species, and designated Nocardia sp. No. C-14482. In the present specification, Nocardia sp. No. C-14482 is briefly referred as strain No. C-14482.

Strain No. C-14482 has been deposited in the following culture collections with the accession numbers indicated. Institute for Fermentation, Osaka (IFO) Japan, IFO-13725; Fermentation Research Institute, Agency of Industrial Science and Technology (FERM), Japan FERM-P No. 4130; The American Type Culture Collection (ATCC), U.S.A., ATCC-31309.

C-14482 $A_1$-producing strain is liable, as observed generally in microorganism of the genus Nocardia, to undergo variations and mutations, whether spontaneously or under the influence of a mutagen. For example, the many variants of the strain which are obtainable by irradiation with X-rays, gamma rays, ultraviolet light, etc., by monocell isolation, by culture on media containing various chemicals, or by any other mutagenic treatment, as well as the mutants spontaneously derived from the strain, should not be considered to represent any other distinct species but, rather, any of such variants and mutants, only if capable of elaborating C-14482 $A_1$ may be invariably utilized for the purposes of this invention. By way of example, subjecting C-14482 $A_1$-producing strain to various mutagenic treatments yields variants which produce light yellowish to light yellowish brown or brown soluble pigments, variants which give colorless vegetative mycelia, variants which give reddish brown to orange red vegetative mycelia, variants which give yellowish green substrate mycelia or soluble pigments, variants which give abundant aerial mycelia which are white in color or variants whose mycelia are ready to be fragmented.

The medium employed for the cultivation of the C-14482 $A_1$-producing strain may be whichever of a liquid and a solid medium only if it contains nutrients which the strain may utilize, although a liquid medium is preferred for high-production purposes. The medium may comprise carbon and nitrogen sources which C-14482 $A_1$-producing strain may assimilate and digest, inorganic matter, trace nutrients, etc. As examples of said carbon sources there may be mentioned glucose, lactose, sucrose, maltose, dextrin, starch, glycerol, mannitol, sorbitol, fats and oils (e.g. soybean oil, lard oil, chicken oil, etc.), n-paraffins and so forth. The nitrogen sources may for example be meat extract, yeast extract, dried yeast, soybean meal, corn steep liquor, peptone, cottonseed flour, spent molasses, urea, ammonium salts (e.g. ammonium sulfate, ammonium chloride, ammonium nitrate, ammonium acetate, etc.) and so forth. The medium may further contain salts of sodium, potassium, calcium, magnesium, etc., salts of iron, manganese, zinc, cobalt, nickel, etc., salts of phosphoric acid, boric acid, etc. and organic acid salts such as acetates and propionates. Further, the medium may contain, as added, various amino acids (e.g. glutamic acid, aspartic acid, alanine, lysine, methionine, proline, etc.), peptides (e.g. dipeptides, tripeptides, etc.), vitamins (e.g. $B_1$, $B_2$, nicotinic acid, $B_{12}$, C, etc.), nucleic acids (e.g. purine, pyrimidine and derivatives thereof) and so forth. For the purpose of adjusting the pH of the medium, there may be added an inorganic or organic acid, alkalis, buffer or the like. Suitable amounts of oils, fats, surfactants, etc. may also be added as antifoams.

The cultivation may be conducted by any of the stationary, shake, submerged aerobic and other cultural methods. For high production runs, submerged aerobic culture is of course preferred. While the conditions of culture depends upon the conditions and compositions of medium, the strain, cultural method and other factors, it is normally preferable to carry out incubation at 15° to 35° C. preferably 20° to 32° C., with an initial pH of about 5.0 to 9.0, preferably about 7.0. Particularly desirable is a temperature from 25° to 28° C. in an intermediate stage of cultivation, with an initial pH of 6.5 to 7.5. While the incubation time also depends on the same factors as mentioned above, it is advisable to continue the incubation until the titer of the desired antibiotic becomes maximal. In the case of shake culture or aerobic submerged culture in liquid medium, the time required normally ranges from about 3 to 8 days.

From the culture broth obtained in the above method, Antibiotic C-14482 $A_1$ can be advantageously isolated by procedures which are normally utilized in the recovery of metabolites from microbial culture. For example, because Antibiotic C-14482 $A_1$ is weakly basic, it can be isolated by a suitable combination of procedures utilizing this property. Thus, since Antibiotic C-14482 $A_1$ occurs primarily in the liquid phase of the culture broth, the broth is first filtered to remove the mycelium and the filtrate is neutralized or made weakly basic. Then, the organic solvents more or less immiscible with water may be utilized to isolate the antibiotic. Such organic solvents include, among others, halogenated hydrocarbons (e.g. chloroform, methylene chloride), fatty acid esters (e.g. ethyl acetate, butyl acetate), ketones (e.g. methyl isobutyl ketone), alcohols (e.g. butyl alcohol, isobutyl alcohol), etc. Antibiotic C-14482 A$_1$ thus extracted by a water-immiscible organic solvent can then be transferred into a water phase by means of a dilute aqueous solution of mineral acid, organic acid or an acidic buffer solution and be thus purified.

Antibiotic C-14482 A$_1$ as it occurs in the cells can be extracted from the filtered cells with a water-miscible organic solvent such as acetone or methanol, with a dilute aqueous solution of mineral acid or with a mixture thereof.

In certain cases, the culture broth including the cells may as such be made weakly acidic and stirred with a water-soluble organic solvent such as acetone or methanol, the mixture be filtered, the filtrate be concentrated under reduced pressure, the acetone or methanol be distilled off and the residual aqueous solution be treated as described in connection with the filtrate of the cultured broth.

An alternative procedure for recovering Antibiotic C-14482 A$_1$ from the filtrate of the cultured broth comprises adsorbing the activity with an adsorbent and eluting it off with a suitable solvent. As examples of the adsorbent which may be thus employed, there may be mentioned activated carbon, non-ionic exchange resin such as Amberlite XAD-2 (Rohm and Haas Co., U.S.A.), Diaion HP-10 (Mitsubishi Chemical Industries, Limited, Japan), etc. As preferred examples of eluant, there may be mentioned aqueous alcohols, e.g. aqueous methanol, aqueous butanol, etc.; aqueous acetone; or those aqueous media as previously made acidic by the addition of dilute mineral acid or the like, although Antibiotic C-14482 A$_1$ may be eluted with an organic solvent such as ethyl acetate or chloroform.

It is also possible to isolate Antibiotic C-14482 A$_1$ by, taking advantage of its basic property, adsorbing it on a cation exchange resin once and desorbing it with an eluant.

As examples of said cation exchange resin, there may be mentioned Amberlite IRC-50, Amberlite IR-120 (Rohm and Haas Co., U.S.A.), Dowex-50 (Dow Chemical Co., U.S.A.) and CM-Sephadex C-25 (Pharmacia Co., Sweden).

To elute the activity from the resin, use may be made of a dilute aqueous solution of mineral acid, a solution of a salt such as sodium chloride, ammonium formate or the like, a dilute aqueous solution of alkali or a mixture of such a solution with a water-soluble organic solvent such as methanol, acetone or the like. By a suitable combination of the above-described purification procedures the contemplated antibiotic product can be obtained in fairly high purity grade. To obtain a highly purified product, such adsorbent materials as silica gel (Merck, Germany), alumina (Merck, Germany), Sephadex LH-20 (Pharmacia, Sweden), etc. may be employed. As examples of the developing solvent there may be mentioned the solvents which are normally employed for the separation of organic compounds; for example, halogenated hydrocarbons (e.g. chloroform, methylene chloride), alcohols (e.g. methanol, ethanol), mixtures thereof (e.g. mixture of chloroform with methanol) and mixtures of esters (e.g. ethyl acetate) with alcohols for instance.

For the purpose of further purification, methods utilizing differences in the distribution coefficient, methods utilizing certain adsorbents, etc. may be mentioned.

The methods utilizing differences in the distribution coefficient include the distribution method which depends on the difference of coefficients between two solvents forming immiscible phases, the counter-current distribution method and the partition chromatography using cellulose powder as the support material, for instance.

When partitioned between chloroform and water at pH 8.0, C-14482 A$_1$ is transferred into the chloroform layer. As to the adsorption method, in which silica gel, for instance, is used as the adsorbent, C-14482 A$_1$ is first adsorbed on a column of silica gel (Merck, Germany) and, then, eluted with a solvent mixture of chloroform and methanol. Subjecting the resultant crude product to thin-layer chromatography with a solvent system of ethyl acetate and methanol for instance yields a pure substance of C-14482 A$_1$.

Antibiotic C-14482 A$_1$, obtained in Example 3 and 4 has the following properties.

Figure 2:
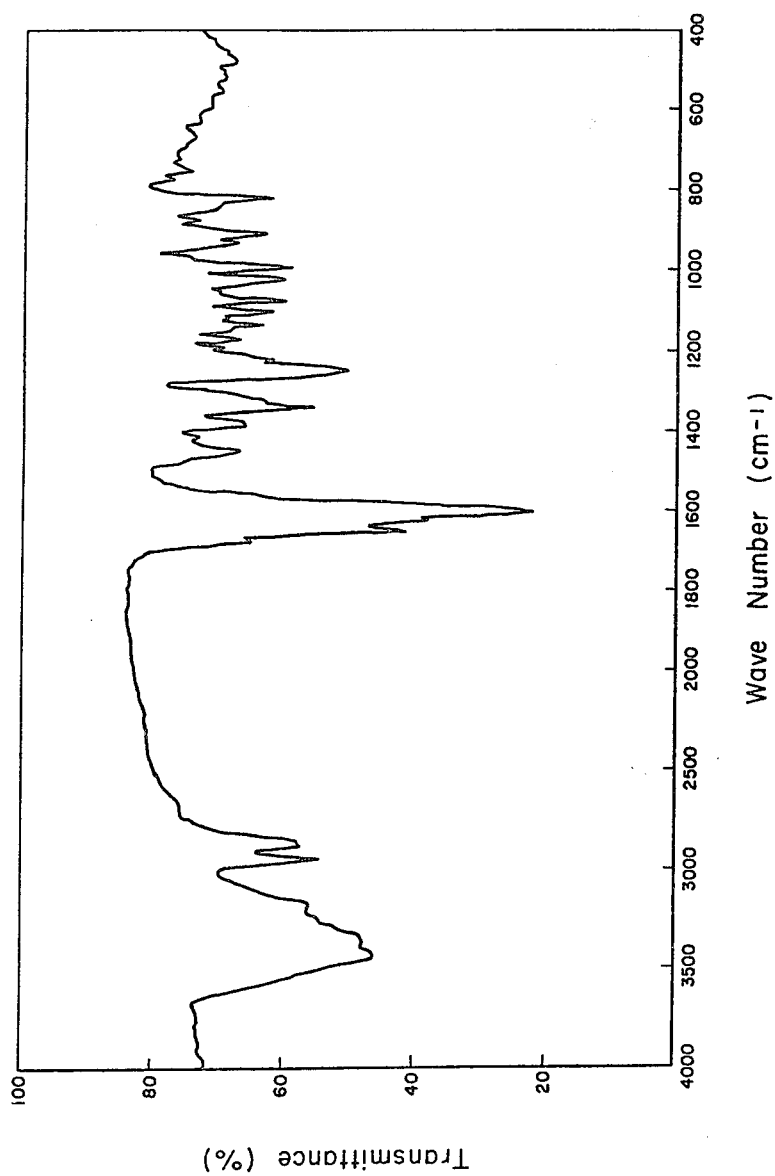

(1) Elemental analysis: (%): C, 58.02, 59.18; H, 5.84, 5.70; N, 16.32, 17.14.
(II) Melting point: Not less than 300° C.
(III) Specific rotation: $[\alpha]_D^{24.5} + 150° \pm 30°$ (c=0.05, ethanol)
(IV) Ultraviolet absorption spectrum: (cf. FIG. 1)
  $\lambda_{max}^{MeOH}$ (E$_{1\ cm}$1%) 214 nm±2 (503±50)
  $\lambda_{max}^{MeOH}$ (E$_{1\ cm}$1%) 281 nm±2 (209±10)
  $\lambda_{max}^{MeOH}$ (E$_{1\ cm}$1%) 498 nm±2 (46.0±5)
(V) Infrared absorption spectrum (KBr): (cf. FIG. 2)
  Principal peaks: (cm$^{-1}$) 3430, 3175, 2940, 2890, 2850, 1680, 1650, 1625, 1600, 1455, 1390, 1345, 1250, 1170, 1140, 1110, 1075, 1025, 995, 935, 910, 825
(VI) Solubility:
  Practically insoluble: Hexane, petroleum ether.
  Sparingly soluble: Ethanol, butanol, ethylacetate, water
  Soluble: Methanol, chloroform
(VII) Color reactions:
  Negative: Sakaguchi reaction, Barton reaction.
  Potassium permanganate is decolorized.
(VIII) Acidity, neutrality or basicity:
  Weakly basic.
(IX) Color of crystals: Dark red to reddish brown.
(X) Molecular weight: 4.6×10$^2$ (measured by Vapor pressure osmometry, in CH$_3$COOC$_2$H$_5$).
(XI) Stability: Between pH 3.0 and pH 8.0, stable at room temperature for 24 hours. Between pH 3.0 and pH 5.0, stable even at 80° C. for 1 hour; at pH 6, slightly unstable when heated at 80° C. for 1 hour; and at pH 7 to 8, fairly unstable.
(XII) Thin-layer chromatography: silica gel (Spot Film f, Tokyo Kasei Co., Japan):
  Chloroform-methanol (9:1): Rf 0.52
  Ethyl acetate-methanol (10:1): Rf 0.38
(XIII) Formation of salts: Being a basic substance, C-14482 A$_1$ forms water-soluble salts with such acids as hydrochloric acid, sulfuric acid, phosphoric acid, tartaric acid, glucuronic acid, etc. and forms sparingly soluble salts with such acids picric acid, picrolonic acid, etc.

As the broad spectrum antibiotics whose crystals have red to reddish purple color, Mitomycin [T. Hata et al. The Journal of Antibiotics, Series A, 9, 141(1956)] and Naphthyridinomycin [D. Kluepfel et al. The Journal of Antibiotics 28, 497(1975)] are mentioned. However, the above two antibiotics are clearly different from the present Antibiotic C-14482 A$_1$ in absorptions in the ultraviolet and visible regions, and elemental analysis (especially nitrogen content).

Since there is no known antibiotic that shares with this antibiotic the aforementioned chemical properties (particularly, absorptions in the ultraviolet and visible regions of the spectrum) and biological properties which are described later and, therefore, C-14482 A$_1$ is believed to be a novel substance.

Biological Activity (A) Antimicrobial activity

Trypticase soy agar medium (hereafter TSA; from Baltimore Biological Limited, U.S.A.), TSA supplemented with 3% of glycerol and TSA supplemented with 1% of glucose were employed and the minimal inhibitory concentrations of C-14482 A$_1$ against the bacteria, acid-fast bacteria, fungi and yeasts were determined by the agar dilution method. The results are shown in Table 4.

TABLE 4

Antimicrobial Spectrum of Antibiotic C-14482 A$_1$

| Test organism | Medium | MIC μg/ml |
| --- | --- | --- |
| Escherichia coli K12 IFO 3301 | TSA | 2 |
| Escherichia coli NIHJ | TSA | 5 |
| Proteus vulgaris IFO 3045 | TSA | 10 |
| Proteus morganii IFO 3168 | TSA | 50 |
| Proteus mirabilis IFO 3849 | TSA | 10 |
| Pseudomonas aeruginosa IFO 3080 | TSA | 2 |
| Salmonella typhimurium IFO 12529 | TSA | 2 |
| Salmonella enteritidis IFO 3313 | TSA | 10 |
| Alcaligenes faecalis IFO 13111 | TSA | 1 |
| Enterobacter cloacae IFO 12009 | TSA | 20 |
| Serratia marcescens IFO 3046 | TSA | 50 |
| Bacillus pumilus IFO 3813 | TSA | 2 |
| Bacillus subtilis 6633 IFO 3134 | TSA | 1 |
| Bacillus subtilis PCI 219 IFO 3513 | TSA | 1 |
| Bacillus cereus IFO 3514 | TSA | 2 |
| Bacillus megaterium IFO 12108 | TSA | 1 |
| Bacillus brevis IFO 3331 | TSA | 0.2 |
| Staphylococcus aureus FDA 209P IFO 12732 | TSA | 1 |
| Staphylococcus aureus OE-R | TSA | 1 |
| Staphylococcus aureus 4R | TSA | 1 |
| Sarcina lutea IFO 3232 | TSA | 1 |
| Mycobacterium avium IFO 3143 | TSA . Gly | 10 |
| Mycobacterium avium SM-R | TSA . Gly | 20 |
| Mycobacterium avium NM-R | TSA . Gly | 20 |
| Mycobacterium smegmatis | TSA . Gly | 5 |
| Mycobacterium phlei | TSA . Gly | 5 |
| Mycobacterium sp. 607 | TSA . Gly | 10 |
| Aspergillus niger IFO 4066 | TSA . Glu | >100 |
| Penicillium chrysogenum IFO 4626 | TSA . Glu | >100 |
| Trichophyton rubrum IFO 5467 | TSA . Glu | >100 |
| Saccharomyces cerevisiae IFO 0209 | TSA . Glu | >100 |
| Candida albicans IFO 0583 | TSA . Glu | >100 |

TSA: Trypticase soy agar
TSA . Gly: Trypticase soy agar supplemented with 3% glycerol
TSA . Glu: Trypticase soy agar supplemented with 1% glucose
OE-R: Oleandomycin-erthromycin resistant mutant in vitro
4R: Tetracycline-streptomycin-chloramphenicol-erythromycin resistant mutant in vitro
SM-R: Streptomycin resistance
NM-R: Neomycin resistance
IFO number: The accession numbers of Institute for Fermentation, Osaka, Japan Plasmid R 100, R 100-1 or F was transmitted to *Escherichia coli* CRT 46, a mutant carrying a thermosensitive chromosome gene, dna A, for the initiation of DNA replication (Hirota et al: Journal of Molecular Biology 35, 175('68)) and the in vitro nalidixic acid-resistant mutant thereof, and thermoresistant revertants (Hfr strains) TE33, TE82 and TE120 were obtained by the method of Nishimura et al. (Journal of Molecular Biology 55, 441('71)). The growth inhibitory activity of Antibiotic C-14482 A$_1$ was assayed against these strains *Escherichia coli* by the broth dilution technique of Yoshikawa et al. [(Antimicrobial Agents and Chemotherapy 5, 362('74)]. The spontaneous thermoresistant revertants TE 144 and TE 146 were employed as controls. Growth was evaluated by absorbance at 600 nm and the growth ratio was calculated fron the ratio of absorbance for the dosed group to that for the undosed group.

TABLE 5

| Test strain | Temperature | Ratio of growth | |
| --- | --- | --- | --- |
| | | 0.0625 μg/ml | 0.125 μg/ml |
| TE 33 | 32° C. | 0.974 | 0.974 |
| | 42° C. | 0.548 | <0.032 |
| TE 82 | 32° C. | 1.019 | 1.000 |
| | 42° C. | 0.353 | 0.029 |
| TE120 | 32° C. | 1.000 | 1.000 |
| | 42° C. | 0.029 | <0.029 |
| TE144 | 32° C. | 0.983 | 1.000 |
| | 42° C. | 0.897 | 0.846 |
| TE146 | 32° C. | 0.981 | 0.981 |
| | 42° C. | 0.912 | 0.294 |

TE 33 CRT 46 nal' R 100 Hfr
TE 82 CRT 46 R100-1 Hfr
TE120 CRT 46 FHfr
TE144 CRT 46 Spontaneous thermoresistant revertant
TE146 CRT 46 nal' Spontaneous thermoresistant revertant (B) Toxicity In an acute toxicity test with mice (CF#1, male, 4-week old), a solution of C-14482 A$_1$ in physiological saline was intraveneously administered. The estimated LD$_{50}$ of this antibiotic was about 5 mg/kg.

As shown in Table 4, Antibiotic C-14482 A$_1$ has strong inhibitory activity against gram-negative, gram-positive and acid-fast bacteria. Therefore, the antibiotic C-14482 A$_1$ is useful as germicides or disinfectants.

Furthermore, the results reported in Table 5 show that this antibiotic is of value as an agent for eliminating R plasmids as well as a seemingly strong nucleic acid synthesis inhibitor and, accordingly, suggest that the present product is of use as an antitumor drug.

Antibiotic C-14482 A$_1$ can be used as germicides, disinfectants or drugs for external application, for example in the disinfection of dining ware, surgical instruments, bird cages, human hands, etc. When the antibiotic is used as a germicide, bactericide or disinfectant against bacteria such as those mentioned in Table 4, it can be used as a liquid preparation which may be prepared, for example by dissolving 10 mg of the antibiotic in 1000 to 2000 ml of water. To use this antibiotic as a drug for external application, it can be formulated into an ointment, for instance, by admixing 0.5 mg of C-14482 A$_1$ evenly with 10 g of white petrolatum.

For example, this antibiotic can be used, in a form of ointment containing 0.5 mg. of C-14482 A$_1$ with 10 g of white petrolatum for topical application to the prevention or treatment of fester of a wound caused by *Staphylococcus aureus* or by mixed infection with the microorganisms mentioned in Table 4 on a human hand by applying 0.02 g. to 0.2 g. of the ointment to the wound four times a day.

In another example, this antibiotic can be utilized in a form of liquid containing 10 mg. of C-14482 A$_1$ in 1000 to 2000 ml of water in the disinfection by dipping dining ware, surgical instruments, bird cages or human hands into the liquid for about 10 minutes.

When administered to mice inoculated with leukaemia P388, C-14482 A$_1$ inhibits multiplication of the tumor cells and has potent life-span extending effects.

Therefore, C-14482 $A_1$ is also useful as an antitumor agent for the treatment of tumor cells in mammals (e.g. mouse, rat, man).

The following examples are further illustrative of this invention.

In the examples, "part(s)" is based on weight unless otherwise noted and the relationship between "part(s)" and "part(s) by volume" corresponds to that between "gram(s)" and "milliliter(s)", and "%" is based on "weight/volume" unless otherwise noted. In the following examples percents of aqueous acetone and aqueous methanol in all occurrences are based on volume/volume.

EXAMPLE 1

A culture of Antibiotic C-14482 $A_1$-producer Nocardia sp. No.C-14482 (IFO 13725, FERM-P No. 4130, ATCC 31309) on a yeast extract-malt extract-agar slant was used to inoculate a 200 parts by volume of Erlenmeyer flask containing 40 parts by volume of a seed culture medium (pH 7.0) composed of 2% glucose, 3% of soluble starch, 1% of soybean flour, 1% of corn steep liquor, 0.5% of peptone, 0.3% of NaCl and 0.5% of $CaCO_3$, and shake culture was carried out on a rotary shaker at 28° C. for 48 hours, whereby a seed culture was obtained.

A 0.5 part by volume portion of this seed culture was transferred to a Erlenmyer flask of 200 parts by volume capacity containing 40 parts by volume of a fermentation medium (pH 7.0) composed of 5% of dextrin, 3% of soybean flour, 0.1% of peptone and 0.5% of $CaCO_3$, which was then incubated on a rotary shaker at 28° C. for 90 hours. This broth was assayed by agar dilution method against *Staphylococcus aureus* FDA 209 P and *Proteus mirabilis* IFO 3849 as test organisms using C-14482 $A_1$ as the standard. The titer thus found was 50 $\mu$g/ml.

EXAMPLE 2

A 10 part by volume portion of the seed culture obtained in Example 1 was transferred to a Sakaguchi flask of 2,000 parts by volume capacity containing 500 parts by volume of a seed culture medium similar to that prepared in Example 1 and the inoculated medium was cultivated at 28° C. for 48 hours. One thousand parts by volume of the culture were inoculated into $100 \times 10^3$ parts by volume of the seed culture medium as above in a fermentation tank of $200 \times 10^3$ parts by volume capacity. The medium was incubated at 28°C. for 48 hours, with aeration at the rate of $100 \times 10^3$ parts by volume/min. and agitation at 200 r.p.m., whereby a seed culture was obtained. This seed culture was transferred to a $2,000 \times 10^3$ parts by volume stainless steel-tank containing $1,000 \times 10^3$ parts by volume of a fermentation medium described in Example 1, the inoculum size used being 10% and incubation was carried out at 28° C. for 90 hours, with aeration at the rate of $1,000 \times 10^3$ parts by volume/min., agitation at 150 r.p.m. ($\frac{1}{3}$ DT) and an internal pressure of 1 kg/cm$^2$. The resultant broth showed a titer of 20 $\mu$g/ml as assayed in the same manner as described in Example 1.

The above broth was adjusted to pH 5.0 and filtered by the filter press with $30 \times 10^3$ parts of Hyflo-Supercel (Johns Manville Co., U.S.A.). The filtrate ($880 \times 10^3$ parts by volume) was brought to pH 8.0 and passed through a column of $100 \times 10^3$ parts by volume of Amberlite XAD-2. The column was washed with $300 \times 10^3$ parts by volume of water and, then, elution was carried out with $250 \times 10^3$ parts by volume of 50% aqueous acetone.

The eluate was distilled under reduced pressure to remove the acetone and the residual aqueous solution was adjusted to pH 6 and adsorbed on a column of $60 \times 10^3$ parts by volume of Amberlite IRC-50 (H-form) After the column was washed with $180 \times 10^3$ parts by volume of water, eluation was carried out with $180 \times 10^3$ parts by volume of 0.2 N-hydrochloric acid. The eluate was brought to pH 6.0 and concentrated under reduced pressure. The concentrate ($30 \times 10^3$ parts by volume) was adjusted to pH 6.0 and was adsorbed on a column of $15 \times 10^3$ parts by volume of Amberlite XAD-2, and the column was washed with $45 \times 10^3$ parts by volume of water and elution was carried out with $60 \times 10^3$ parts by volume of 50% aqueous acetone. The eluate was adjusted to pH 5-6 and concentrated under reduced pressure to about 1000 parts by volume.

To the concentrate was added $9 \times 10^3$ parts by volume of acetone, whereupon 124 parts of crude product I were obtained.

The mother fluid was further distilled to remove the acetone and the residue was lyophilized, whereby 36 parts of crude product II were obtained.

In 450 parts by volume of water were dissolved 4.5 parts of crude product II and the solution was brought to pH 8 with dilute aqueous $NH_4OH$ and extracted repeatedly (4-5 times) with 225 parts by volume of $CHCl_3$. The $CHCl_3$ extracts were combined and the activity was transferred to an aqueous layer with use of 300 parts by volume of 1/200 N-hydrochloric acid. The wine-colored aqueous layer was adjusted to pH 5.5-6.0, concentrated under reduced pressure, adjusted to pH 6.0 and run onto a column of 170 parts by volume of Diaion HP-10(non-ion-exchange resin, Mitsubishi Chemical Industries, Limited, Japan). The column was washed with 500 parts by volume of water and 700 parts by volume of 30% aqueous methanol in that order and, then, elution was carried out with 700 parts by volume of 80% aqueous methanol, whereby a wine-colored antibiotic activity was obtained.

The eluate was adjusted to pH 6, concentrated under reduced pressure and lyophilized. By the above procedure there was obtained 0.185 part of dark red powders. A 0.155 part portion of this product was subjected to thin-layer chromatography on silica gel (Merck, Germany, $HF_{254}$) (solvent: $CHCl_3$—MeOH=10:1), and fractions, whose Rf value is 0.45, were collected and extracted with methanol, whereby 0.024 part of $A_1$ fraction was obtained. 0.02 part of the above $A_1$ fraction was purified by the thin-layer chromatography on silica gel (Merck, Germany $HF_{254}$) with a solvent system of ethyl acetate-methanol(10:1), whereby the purified $A_1$ fraction (0.009 part) was obtained by extraction with methanol from the corresponding band (Rf 0.33) to $A_1$. $E_{1cm}^{1\%}$ of this C-14482 $A_1$ in methanol was 41.3 at 498 nm.

EXAMPLE 3

$850 \times 10^3$ parts by volume of a culture broth filtrate prepared by a procedure similar to that described in Example 2 was passed through a column of $85 \times 10^3$ parts by volume of Amberlite XAD-2, after the column was washed with water ($255 \times 10^3$ parts by volume), elution was carried out with $210 \times 10^3$ parts by volume of 50% aqueous acetone. The eluate was distilled to remove the acetone and the residual aqueous solution was adjusted to pH 6.0 and adsorbed on a column of $51 \times 10^3$ parts by volume of Amberlite IRC-50 (H-form). After the column was washed with $150 \times 10^3$ parts by volume of water, elution was carried out with $150 \times 10^3$ parts by volume of 0.2 N-HCl. The eluate was adjusted to pH 5.5-6.0, concentrated under reduced pressure to about $50 \times 10^3$ parts by volume and adsorbed on a column of $12 \times 10^3$ parts by volume of Amberlite XAD-2. The column was washed with water and elution was carried out with $18 \times 10^3$ parts by volume of 50% aqueous acetone. The eluate was adjusted to pH 5.5-6.0, concentrated under reduced pressure and lyophilized. By the above procedure were obtained 118.3 parts of crude powders of C-14482 $A_1$.

In $9 \times 10^3$ parts by volume of water were dissolved 90 parts of the above crude powders and the solution was brought to pH 8.0 with dilute aqueous $NH_4OH$ and extracted with $3 \times 10^3$ parts by volume of n-butanol three times.

The extracts were combined and transferred twice into aqueous layers with $3 \times 10^3$ parts by volume of N/200 HCl. The water layers were pooled, adjusted to pH 6. The n-butanol was removed and the residual aqueous solution (pH 6) was poured onto a column of $4.5 \times 10^3$ parts by volume of Diaion HP-10(Mitsubishi Chemical Industries Limited). The column was washed with $13.5 \times 10^3$ parts by volume of water and $9 \times 10^3$ parts by volume of 30% aqueous methanol in that order and elution was carried out with $13.5 \times 10^3$ parts by volume of 80% aqueous methanol, whereby 3.45 parts of an $A_1$-rich fraction (F-1) were obtained.

The above $A_1$-rich fraction (F-1) (3.0 parts) was adsorbed on a column of 150 parts of silica gel (Merck, Germany) and elution was carried out with solvent mixtures of chloroform and methanol, 50:1 ($1.3 \times 10^3$ parts by volume), 25:1 ($1 \times 10^3$ parts by volume) and 10:1 ($1 \times 10^3$ parts by volume), in the order mentioned. Finally, elution was carried out with $1 \times 10^3$ parts by volume of methanol.

The elution with a mixture of $CHCl_3$:MeOH(25:1) yielded 0.368 part of an $A_1$-rich fraction. 0.340 Part of the $A_1$-rich fraction was purified by thin-layer chromatography on silica gel (Merck, $HF_{254}$) with a solvent mixture of chloroform and methanol (9:1), whereby 0.109 part of C-14482 $A_1$ was obtained as purified dark red crystalline powders.

Analysis (after dried at 60° C., 30 hours in vacuo): C, 59.18; H, 5.70; N, 17.14.

$\lambda_{max}^{MeOH}$ 498 nm ($E_{1cm}^{1\%}$ 48.3)

EXAMPLE 4

$900 \times 10^3$ parts by volume of a culture broth prepared in the same manner as Example 2 was adjusted to pH 4.0 with 4 N-$H_2SO_4$, followed by addition of $800 \times 10^3$ parts by volume of acetone. The mixture was stirred for 3 hours. $30 \times 10^3$ parts of Hyflo-Supercel (Johns Manville Co., U.S.A.) were added and were filtered by the filter press. The filtrate was adjusted to pH 5.5 and concentrated under reduced pressure to $800 \times 10^3$ parts by volume. The acetone was removed and the residual aqueous solution was adjusted to pH 6.0 and passed through a column of $90 \times 10^3$ parts by volume of Diaion HP-10. The column was washed with $270 \times 10^3$ parts by volume of water and elution was carried out with $250 \times 10^3$ parts by volume of 50% aqueous acetone.

The acetone was removed and the residual aqueous solution ($100 \times 10^3$ parts by volume) was adjusted to pH 8.0 and extracted three times with $30 \times 10^3$ parts by volume of iso-butanol. The extracts were pooled and the active substance was transferred twice with $60 \times 10^3$ parts by volume of N/200-HCl into an aqueous layer.

The isobutanol contained in the aqueous layers was removed by distillation at pH 5-6 under reduced pressure. The residual aqueous solution was adjusted to pH 6.0 and poured onto a column of Diaion HP-10 ($45 \times 10^3$ parts by volume). The column was washed with water and elution was carried out with $135 \times 10^3$ parts by volume of 50% aqueous acetone. The eluate was adjusted to pH B 6, concentrated under reduced pressure and lyophilized. By the above procedure was obtained 82 parts of C-14482 $A_1$-rich crude powders (f-1).

In $1.5 \times 10^3$ parts by volume of water were dissolved 15 parts of the above powders (f-1) and the active substance was extracted four times with 750 parts by volume of $CHCl_3$ at pH 8.0 (adjusted with dil. $NH_4OH$) and transferred to 750 parts by volume of 1/200 N-HCl twice. The water layers were combined and, at pH 6, concentrated under reduced pressure. The concentrate was passed onto a column of 400 parts by volume of Diaion HP-10 and after the column was washed with $1.2 \times 10^3$ parts by volume of water and $1.2 \times 10^3$ parts by volume of 30% aqueous methanol in that order, elution was carried out with $1.2 \times 10^3$ parts by volume of 80% aqueous methanol. The eluate was adjusted to pH 6, concentrated under reduced pressure and lyophilized. By the above procedure there was obtained 0.393 part of dark reddish brown powders rich in $A_1$. A 0.375 part portion of this powdery product was purified by silica gel column chromatography and thin-layer chromatography as in Example 2 and 3. In this manner, 0.02 part of C-14482 $A_1$ was obtained as purified dark red crystals.

Analysis (after dried at 60° C., 30 hours in vacuo): C, 58.02; H, 5.84; N, 16.32

$\lambda_{max}^{MeOH}$ 498 nm ($E_{1cm}^{1\%}$ 44.2)

What we claim is:

1. Antibiotic C-14482 $A_1$ which has the following properties:

(I) Elemental analysis: (%) C, 58.02, 59.18; H, 5.84, 5.70; N, 16.32, 17.14;

(II) Melting point: Not less than 300° C.

(III) Specific rotation: $[\alpha]_D^{24.5} +150° \pm 30°$ (c=0.05, ethanol)

(IV) Ultraviolet absorption spectrum:
$\lambda_{max}^{MeOH}$ ($E_{1cm}^{1\%}$) 214 nm$\pm 2(503 \pm 50)$
$\lambda_{max}^{MeOH}$ ($E_{1cm}^{1\%}$) 281 nm$\pm 2(209 \pm 10)$
$\lambda_{max}^{MeOH}$ ($E_{1cm}^{1\%}$) 498 nm$\pm 2(46.0 \pm 5)$ (V) Infrared absorption spectrum (KBr): Principal peaks (cm$^{-1}$) 3430, 3175, 2940, 2890, 2850, 1680, 1650, 1625, 1600, 1455, 1390, 1345, 1250, 1170, 1140, 1110, 1075, 1025, 995, 935, 910, 825

(VI) Solubility:
Practically insoluble: Hexane, petroleum ether
Sparingly soluble: Ethanol, butanol, ethyl acetate, water
Soluble: Methanol, chloroform (VII) Color reactions: Negative: Sakaguchi reaction, Barton reaction, Potassium permanganate declorized, (VIII) Acidity, neutrality or basicity: Weakly basic, (IX) Color of crystals: Dark red to reddish brown, (X) Molecular weight: $4.6 \times 10^2$ (measured by Vapor pressure osmometry in $CH_3COOC_2H_5$).

2. A method for producing Antibiotic C-14482 $A_1$ which comprises cultivating a microorganism which belongs to the genus Nocardia sp. No. C-14482 (ATCC-31309) and is capable of producing Antibiotic C-14482 $A_1$ in a culture medium, whereby Antibiotic C-14482 $A_1$ is elaborated and accumulated in said culture medium and recovering the antibiotic.

* * * * *